(12) United States Patent
Papai

(10) Patent No.: US 6,663,384 B2
(45) Date of Patent: Dec. 16, 2003

(54) VENTING PLATE FOR A CONTAINERIZED CANDLE

(76) Inventor: Tod A. Papai, 2102 Michigan Ave., LaPorte, IN (US) 46350

(*) Notice: Subject to any disclaimer, the term of this patent is extended or adjusted under 35 U.S.C. 154(b) by 2 days.

(21) Appl. No.: 10/352,415

(22) Filed: Jan. 28, 2003

(65) Prior Publication Data

US 2003/0129558 A1 Jul. 10, 2003

Related U.S. Application Data

(63) Continuation-in-part of application No. 10/040,121, filed on Jan. 4, 2002, now Pat. No. 6,382,962.

(51) Int. Cl.⁷ .................................... F23D 3/18
(52) U.S. Cl. ...................... 431/289; 431/291; 362/161
(58) Field of Search ................ 431/289, 288, 431/126, 291, 125; 362/159, 161, 163, 171, 362, 363, 373, 172, 180, 181, 182

(56) References Cited

U.S. PATENT DOCUMENTS

| | | | | | |
|---|---|---|---|---|---|
| 214,238 | A | * | 4/1879 | Butler | 362/312 |
| 569,572 | A | * | 10/1896 | Bourne | 362/182 |
| 592,705 | A | * | 10/1897 | Hamm | 362/182 |
| 698,053 | A | * | 4/1902 | Prahm | 362/182 |
| 813,885 | A | * | 2/1906 | Handlan | 362/182 |
| 878,518 | A | * | 1/1908 | Fresh | 251/17 |
| 1,011,779 | A | * | 12/1911 | Harrington | 362/182 |
| 1,022,821 | A | * | 4/1912 | Briand | 362/182 |
| 1,039,123 | A | * | 9/1912 | Hamm | 362/182 |
| 1,097,464 | A | * | 5/1914 | Prahm | 362/182 |
| 1,540,015 | A | * | 6/1925 | Karlson | 362/182 |
| 1,819,733 | A | * | 8/1931 | Castelli | 362/431 |
| 1,867,420 | A | * | 7/1932 | Root | 431/291 |
| 1,915,622 | A | * | 6/1933 | Sevcik | 431/291 |
| 1,975,496 | A | * | 10/1934 | Barrett, Jr. | 362/161 |
| 2,050,151 | A | * | 8/1936 | Baumer | 362/161 |
| 6,231,336 | B1 | * | 5/2001 | Chen | 431/291 |
| 6,382,962 | B1 | * | 5/2002 | Papai | 431/291 |
| 2002/0058223 | A1 | * | 5/2002 | Papai | 431/288 |

FOREIGN PATENT DOCUMENTS

| | | | | |
|---|---|---|---|---|
| DE | 10825 | * | 1/1880 | 362/161 |
| DE | 588031 | * | 10/1933 | 362/180 |
| DE | 190474 | * | 8/1956 | 362/163 |
| DE | 2618394 | * | 1/1978 | 431/291 |
| DE | 20100017 U1 | * | 8/2001 | 431/291 |
| FR | 1135721 | * | 5/1957 | 362/161 |
| GB | 9744 | * | 6/1896 | 362/182 |
| GB | 170933 | * | 10/1921 | 362/161 |
| JP | 01-215891 | * | 8/1989 | 431/291 |

* cited by examiner

Primary Examiner—Carl D. Price

(57) ABSTRACT

A venting plate for an apothecary jar candle is disclosed, which includes a ceramic venting chassis and decorative three dimensional ornamentation bonded to the chassis. The venting plate with its decorative three dimensional ornamentation can remain atop an apothecary jar candle while burning. The ornamentation is composed of molded poly resin reliefs of various genre and styles. The unique venting chassis provides sufficient thermal insulation to protect the reliefs and provides sufficient laminar air flow within an apothecary jar candle to improve the combustion efficiency and reduce candle smoke. In one embodiment of the venting plate, the ceramic chassis has a flat plate , a cylindrical skirt which extends from the bottom of the flat top and a plurality of mounting feet, which support the chassis atop a jar candle. The mounting feet space the plate above the candle brim to permit the flow of inlet air underneath the venting plate between the plate top and the brim of the candle vessel. The annular baffle extends downward into the mouth of the vessel around the exhaust vent, which redirects the inlet air flow, which enters the candle horizontally from underneath the venting plate, downward along the vessel sidewall.

14 Claims, 9 Drawing Sheets

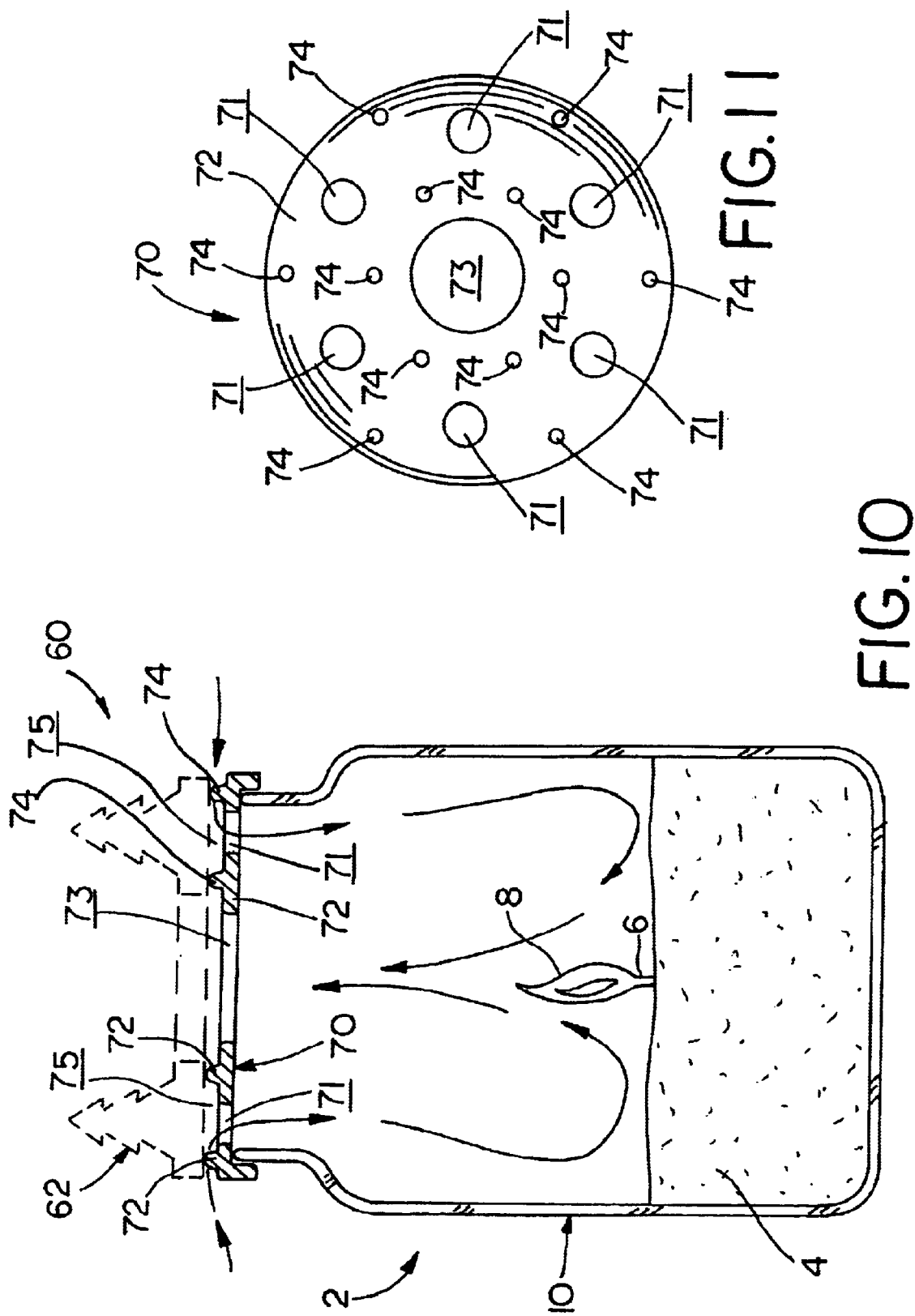

ly polyresin reliefs molded into decorative shapes, scenery,
VENTING PLATE FOR A CONTAINERIZED CANDLE This is a continuation-in-part of U.S. patent application Ser. No. 10/040,121 filed Jan. 4, 2002 now U.S. Pat. No. 6,382,962. This invention relates to a venting plate for containerized candles, which improves the candle's combustion and eliminates candle smoke.

BACKGROUND OF INVENTION

A variety of decorative lids have been developed for containerized or apothecary jar candles. Decorative lids, such as the one manufactured by Our America, Inc. of Agawam, Mass., are ornamented with three dimensional poly resin reliefs molded into decorative shapes, scenery, and figurines. These poly resin reliefs are typically painted to add greater detail and ornamentation. Poly resin reliefs are easily produced and inexpensive. Poly resin reliefs can be produced separately and then simply bonded to a standard jar lid. This type of decorative lid has become widely popular in the candle industry, since the poly resin ornamentation can be changed to suit various genre and styles of decorative and aesthetic tastes. While this type of decorative lid is a popular candle accessory, the lid must be removed when the candle is burnt.

Recently, a new candle accessory for apothecary jar candles has been developed, the venting plate. Venting plates, such as the ones described in U.S. Pat. No. 6,382,962 granted May 7, 2002, are used with apothecary jar candles to improve the combustion efficiency and reduce soot and smoke. Typically venting plates have a central exhaust vent opening and a plurality of peripheral inlet vent openings which are situated to facilitate concentric laminar air flows within the container by separation of the cool inlet air from the hot exhaust air. These venting plates have some aesthetic limitations. The plate is limited to two dimensional ornamentation etched or carved on the surface of the plate. Because this venting plate has multiple openings for both the inlet and exhaust vents, the top surface venting plates cannot be adorned with three dimensional poly resin relief or other ornamentation without obstructing the air flow into and out of the candle. Consequently, this venting plate is limited aesthetically to mere surface ornamentation. In addition, the multiple openings reduce the amount of surface area available for ornamentation.

Consequently, developing a venting plate that can support a decorative poly resin relief would be commercially advantageous. Several practical problems must be addressed in order to combine a venting plate with a decorative poly resin relief for an apothecary jar candle. The venting plate would have to shield the relief from the heat of the candle flame and the hot exhaust air. Exposure to excessive heat could cause the poly resin relief to melt, breakdown or ignite. Consequently, the venting plate must provide sufficient thermal insulation to avoid safety concerns. In addition, the venting plate must provide a large top surface for supporting the relief without obstructing the laminar air flow within the candle.

SUMMARY OF INVENTION

The venting plate of this invention combines the aesthetic ornamentation of three dimensional poly resin reliefs with venting plate technology of apothecary jar candles. The venting plate of this invention employs a two piece design, which includes three dimensional ornamentation bonded to a separate ceramic venting chassis. Different embodiments of the venting plates are disclosed, which utilize different chassis designs.

In one embodiment, the venting chassis has a flat disc shaped plate, a cylindrical skirt which extends from the bottom of the flat top and a plurality of mounting feet, which support the chassis atop ajar candle. The mounting feet space the plate above the candle brim to permit the flow of inlet air between the plate and the brim of the candle jar. The annular baffle extends downward into the mouth of the vessel around the exhaust vent and has six recessed longitudinal furrow or inlet channels, through which the inlet air flow passes into the vessel interior. The baffle redirects the inlet air flow, which enters the candle horizontally from underneath the venting plate, downward along the vessel sidewall. In another embodiment, the venting chassis used the conventional flat venting plate design with inlet openings or venting formed around a central exhaust opening or vent. The venting chassis of this embodiment, however, also has a plurality of raised detent or feet, upon which the ornamentation is mounted. The plurality of feet space the ornamentation above the top surface of the plate to allow inlet air to pass between the plate and the ornamentation and down into the candle interior through the inlet openings.

Both embodiments of the venting chassis have a ceramic composition, which allows three dimensional ornamentation of poly resin composition to adorn the venting plate without affecting its function while atop a burning apothecary jar candle. The ceramic chassis not only provides the venting functions to ensure an efficient combustion and reduce smoke, but is designed to provide thermal insulation for the poly resin relief molded to the chassis. The body of the chassis has sufficient thickness to protect the relief from the heat of the flame. The venting chassis may also include a chimney, which shields the relief form hot exhaust air. In a second embodiment of the venting chassis, the top surface of the chassis has an annular recess that creates an air gap between the chassis and the relief to give additional thermal protection to the ornamentation.

Accordingly, an advantage of this invention is that the venting plate uses ceramic chassis that can support a decorative poly resin relief.

Another advantage is that the venting plate can be adorned with three dimensional figurines and ornamentation, as well as, surface decorations without affecting the operation of the venting plate.

Another advantage is that the venting plate can incorporate a chimney to provide a thermal shield for protecting ornamentation mounted to the surface of the venting plate.

Another advantage is that the venting plate stabilizes the combustion flame and improves the efficiency of the combustion of conventional containerized candles, thereby reducing the smoke produced in the combustion process of containerized candles.

Another advantage is that the venting cover reduces turbulence in containerized candles by separating concentric laminar air flow within the candle container, which enables sufficient ambient air flow directly to the base of the flame.

Another advantage is that the venting plate eliminates the need for peripheral inlet vent openings in the venting plate.

Another advantage is that the venting plate includes an internal baffle for directing inlet air flow downward along the sidewalls of a containerized candle.

Another advantage is that the venting plate is supported atop a containerized candle by a plurality of mounting bosses, which space the plate above the brim of the candle to form an annular inlet vent.

Other advantages will become apparent upon a reading of the following description.

BRIEF DESCRIPTION OF THE DRAWINGS

The preferred embodiments of the invention have been depicted for illustrative purposes only wherein:

FIG. 10 is a side sectional view of a third embodiment of the venting plate of this invention seated atop a cylindrical containerized candle;

FIG. 11 is a top plan view of the venting chassis of the embodiment of the venting plate of this invention shown in FIG. 10;

DESCRIPTION OF THE PREFERRED EMBODIMENT

The preferred embodiments herein described are not intended to be exhaustive or to limit the invention to the precise form disclosed. They are chosen and described to explain the invention so that others skilled in the art might utilize its teachings.

Figure 1:
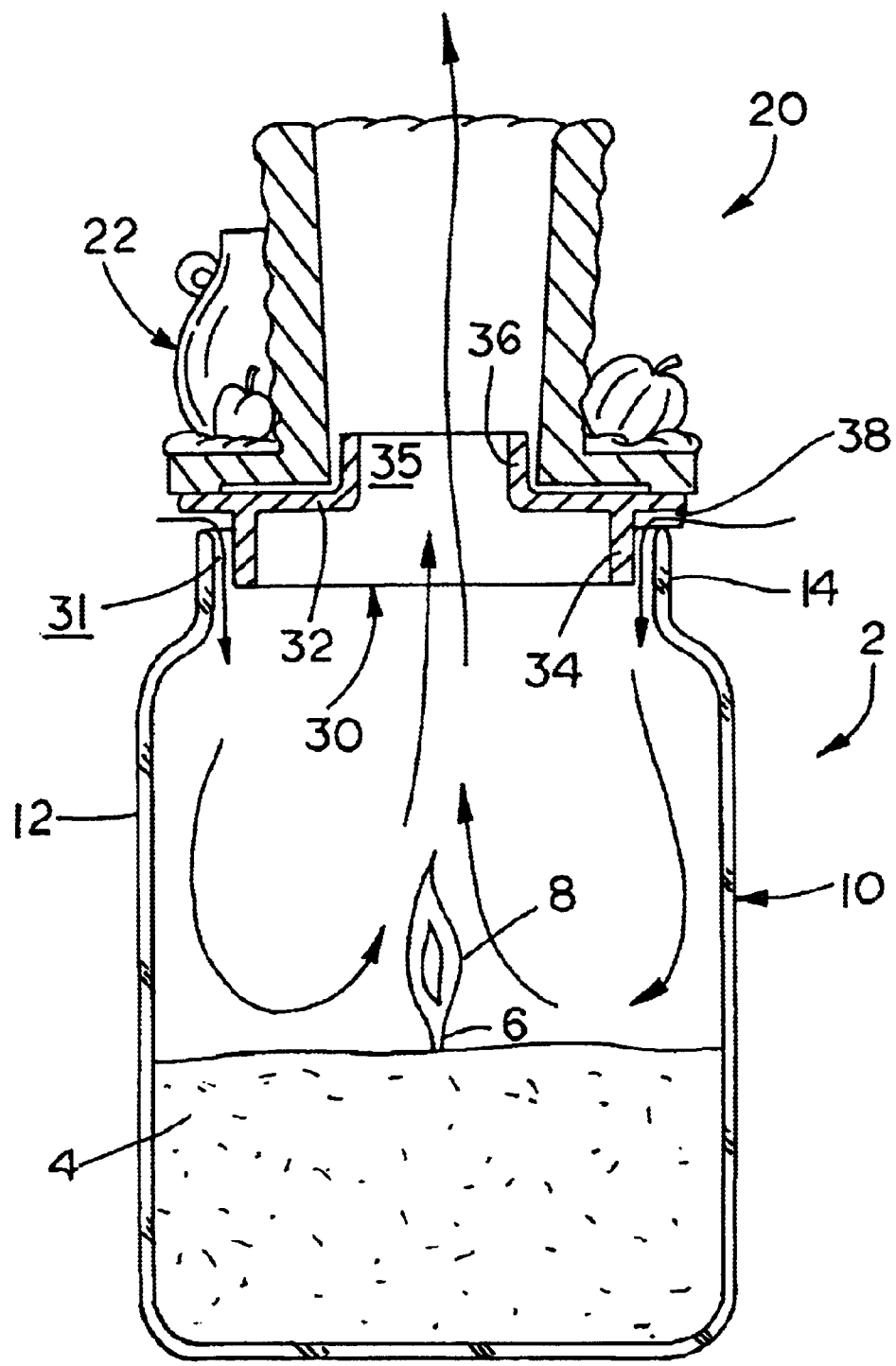
FIG. 1 is a side sectional view of a first embodiment of the venting plate of this invention seated atop a cylindrical containerized candle.

The venting plates of this invention each include a venting chassis and a decorative three dimensional ornamentation. The figures illustrate several different embodiments of the venting plates of this invention each utilizing a variation of venting chassis. The venting plats of this invention are intended for use on conventional apothecary jar candles (designated generally as reference numeral 2). The venting plates are illustrated for descriptive purposes only being used on a conventional cylindrical apothecary jar candle (designated generally as reference numeral 2). The venting plate of this invention is intended to be adapted for use with any apothecary jar candle regardless of shape, wick con- figuration or dimension, and is illustrated with a cylindrical jar candle only for simplicity of explanation and illustration. As shown in FIG. 1, candle 2 includes a quantity of wax 4, and one or more cloth or porous wicks 6 contained inside a transparent or translucent glass jar or vessel 10. Vessel 10 includes sidewalls 12 that terminate in a brim 14 forming an open mouth. The size of vessel 10 and the dimensions of its mouth may vary, as well as, its shape within the scope of this invention. Candle wax 4 fills the bottom portion of vessel 10. One or more wicks 6 are seated within the solid wax. When candle 2 is burning, the heat from flame 8 creates a thin layer of melted candle wax across the top of the solid candle wax, which is drawn up the wicks 6 to feed the flame. Wax 4 is employed in candle 2 as a fuel source and may take any natural unctuous, viscous or solid heat sensitive compound consisting essentially of high molecular weight hydrocarbons or esters of fatty acids. Typically, the candle wax also contains various essential oils to give the wax a pleasant scent and aroma when burned. The gaseous and solid particulate of the essential oils is carried in the combustion exhaust as the wax burns. Ideally, in a clean combustion, soot and smoke are reduced by providing sufficient oxygen to the flame to completely spend the hydrocarbon fuel, while the scent particulate is expelled with the hot exhaust air.

Figure 2:
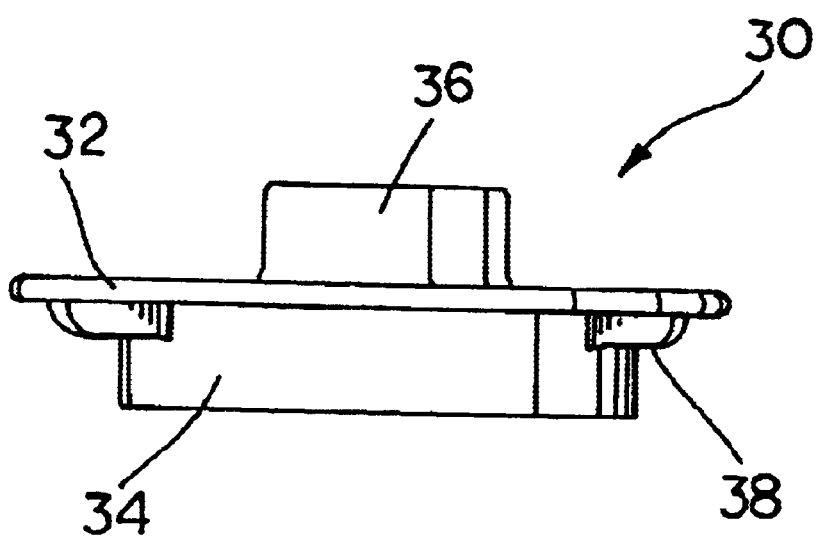
FIG. 2 is a side elevation view of the venting chassis of the embodiment of the venting plate of this invention shown in FIG. 1.
Figure 3:
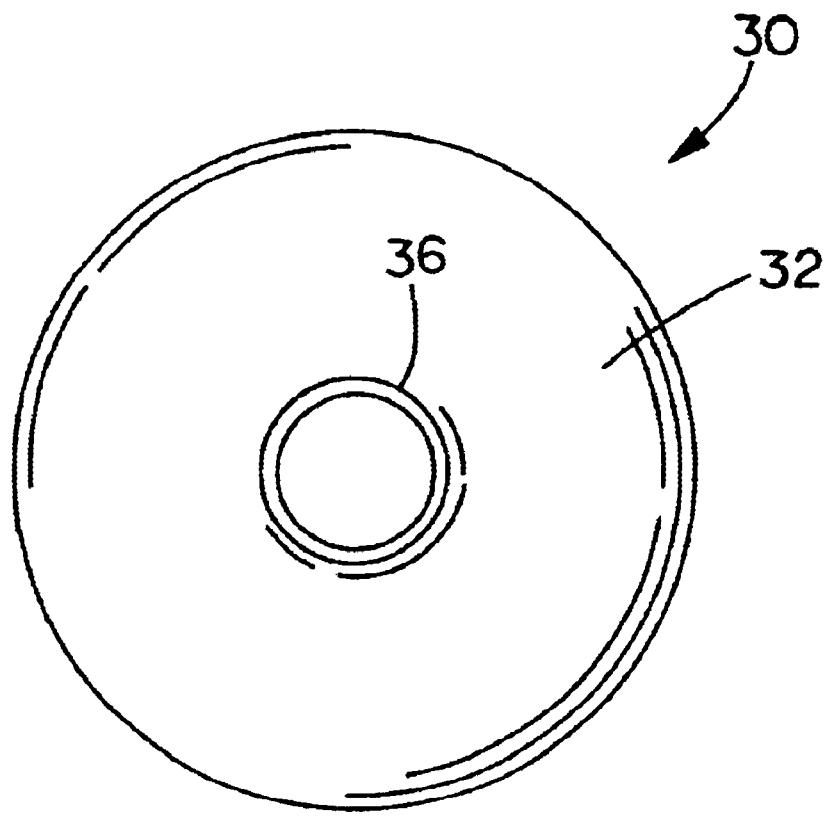
FIG. 3 is a top plan view of the venting chassis of the embodiment of the venting plate of this invention shown in FIG. 1.

FIGS. 1–3 shows the first embodiment of the venting plate of this invention (designated generally as reference numeral 20), which includes generally a ceramic venting chassis 30 and a decorative three dimensional ornamentation or relief 22. Typically, ornamentation 22 takes the form of a molded relief, which can be painted or otherwise adorned. As shown in FIG. 1, ornamentation 22 is molded as a basket with fruit and vegetables positioned around the basket. It should be noted that ornamentation 22' is configured so that it does not obstruct the flow of exhaust air exiting the exhaust vent of the chassis. The relief can be molded from a poly resin material or ceramic. Poly resin reliefs are preferably due to their durability and easy of production. The relief itself can be molded and formed into any aesthetically pleasing shape and configurations. While an integral part of the venting plate, the function of ornamentation is purely aesthetic and does not contribute directly to the operational function of the chassis. As shown, ornamentation 22 is bonded to the top surface of chassis 12 using any suitable heat resistant adhesive.

Venting chassis 30 is constructed of a ceramic material or other material that can be readily formed into a rigid body with thermal insulating properties. Venting chassis 30 includes a flat disc or plate 32, a cylindrical skirt 34 extending from the bottom surface of the plate 32, and a cylindrical chimney 36 that extends from the top surface of the plate around a central exhaust opening 35 in the plate. Plate 32 is illustrated in the figures as a planar circular disc, but may be conical or domed in shape as desired. Likewise, exhaust vent 35 while illustrated as a circular opening may take any shape or configuration without deviating from the teachings of this invention. Typically, the cross sectional area of the exhaust vent 35 is approximately 0.785 square inches (roughly a circular opening having a 1.00 inch diameter), but may range between 0.700–0.900 square inches. This cross sectional area is generally ideal for venting exhaust air from the combustion of conventional four inch diameter apothecary jar candles. Chimney 36 extends at least 0.500 inches above the top surface of plate 32. Skirt 34 extends at least 0.600 inches from the bottom surface of plate 32. The thickness of plate 32 is at least 0.125 inches. This thickness of plate 32 is generally sufficient for the ceramic material to thermally insulate ornamentation 22 from the maximum heat generated by a conventional apothecary jar candle when the flame is at its closest proximity to venting plate 20 atop a candle. Likewise, the thickness of the walls of chimney 36 are preferably at least 0.125 inches.

Three feet 38 extend outward radially from skirt 34 on the bottom surface of plate 32 at equally spaced locations. As shown in FIG. 1, venting plate 20 sits atop of candle 2 supported by mounting feet 38, such that skirt 34 extends downward into mouth 15 of candle 2. Mounting feet 38 support the venting plate atop candle 2 such that the bottom surface of plate 32 is spaced vertically above the brim and that skirt 34 is equally spaced from brim 14. The vertical and horizontal spacing between venting chassis 30 and vessel brim 14 constitutes an annular inlet vent 31 around the periphery of the mouth through which inlet air can enter the candle interior. The cross sectional area of inlet vent 31, that is the vertical and horizontal spacing between the venting chassis and the vessel brim provides sufficient inlet air flow into the candle interior to maintain efficient combustion. As shown in FIG. 1, feet 38 space plate 32 from vessel brim 14 at least 0.125 of an inch. The distance between the skirt and candle brim 14 should be at least 0.063 inches.

Figure 4:
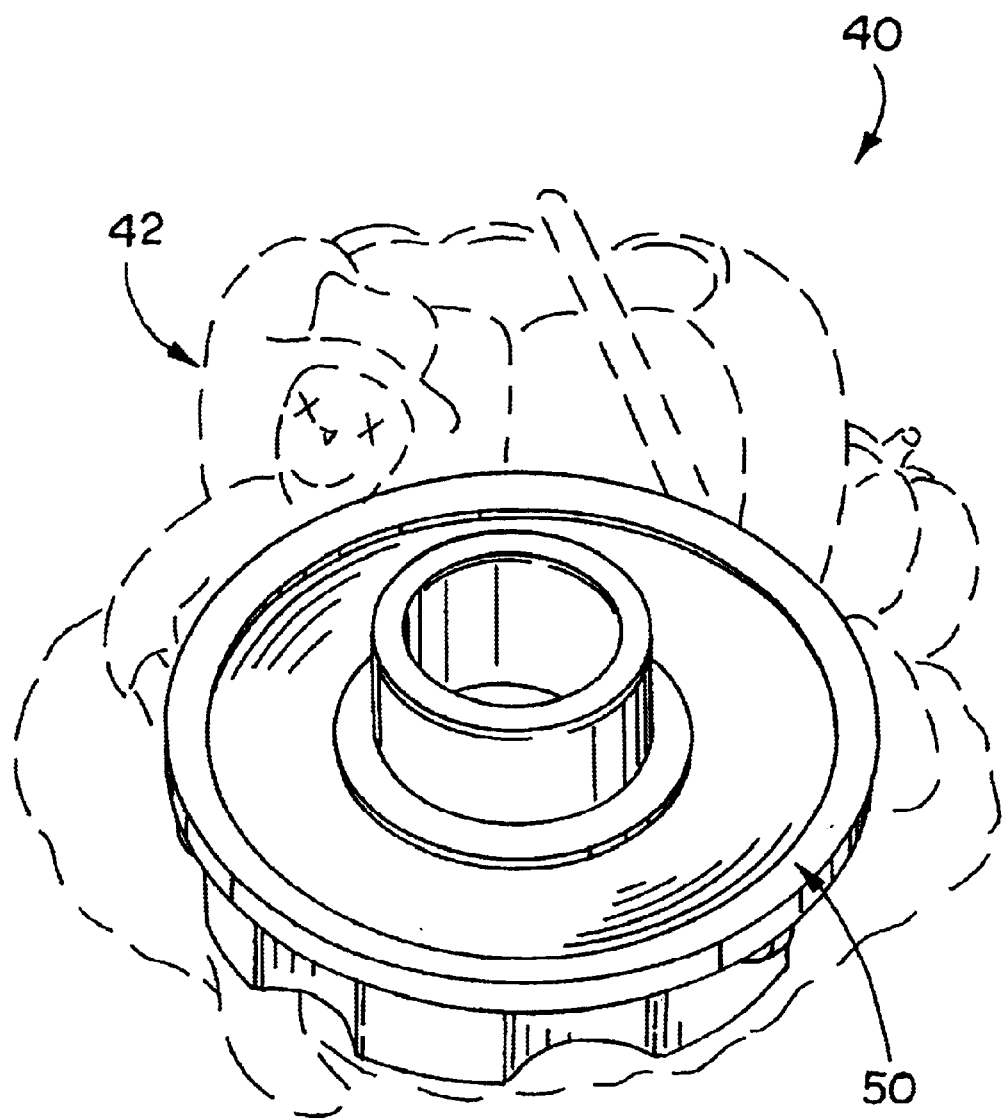
FIG. 4 is a perspective view of a second embodiment of the venting plate of this invention with the ornamentation shown in shadow.
Figure 5:
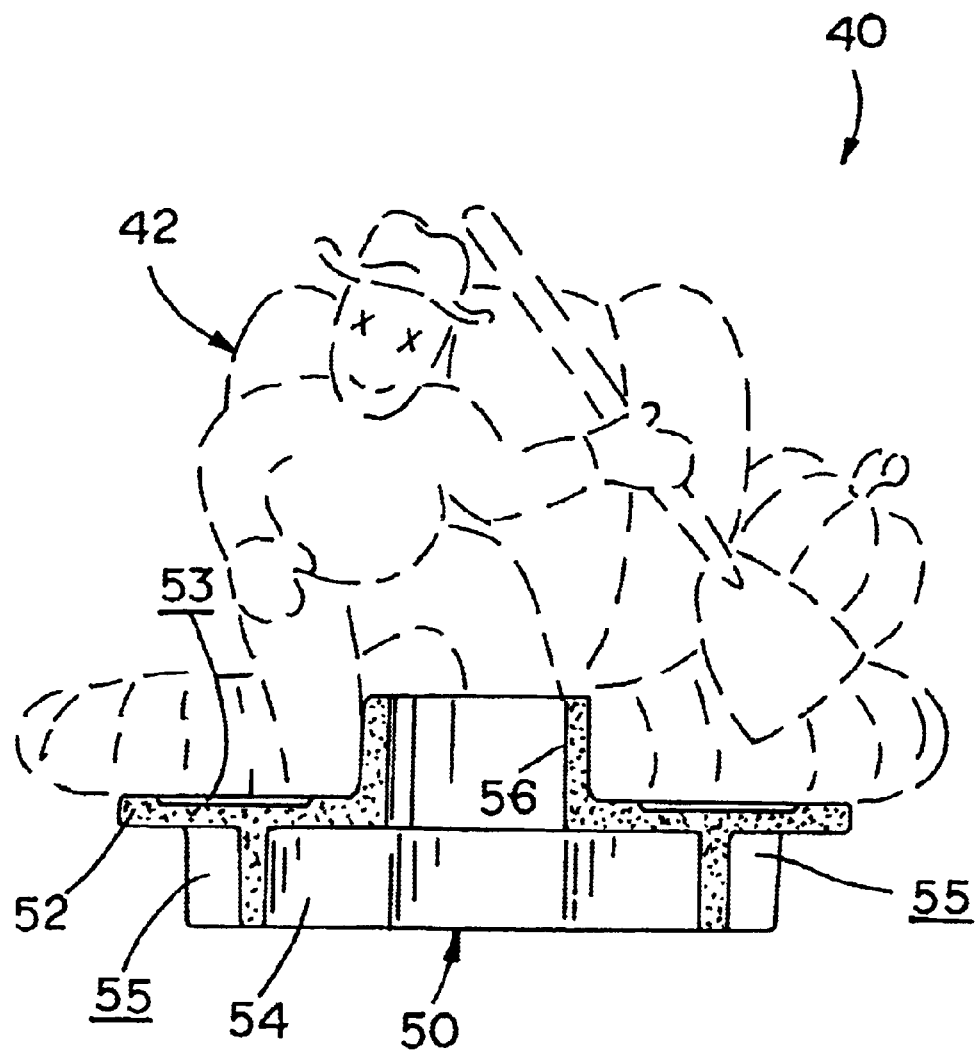
FIG. 5 is a side sectional view of the embodiment of the venting plate of this invention shown in FIG. 4.
Figure 6:
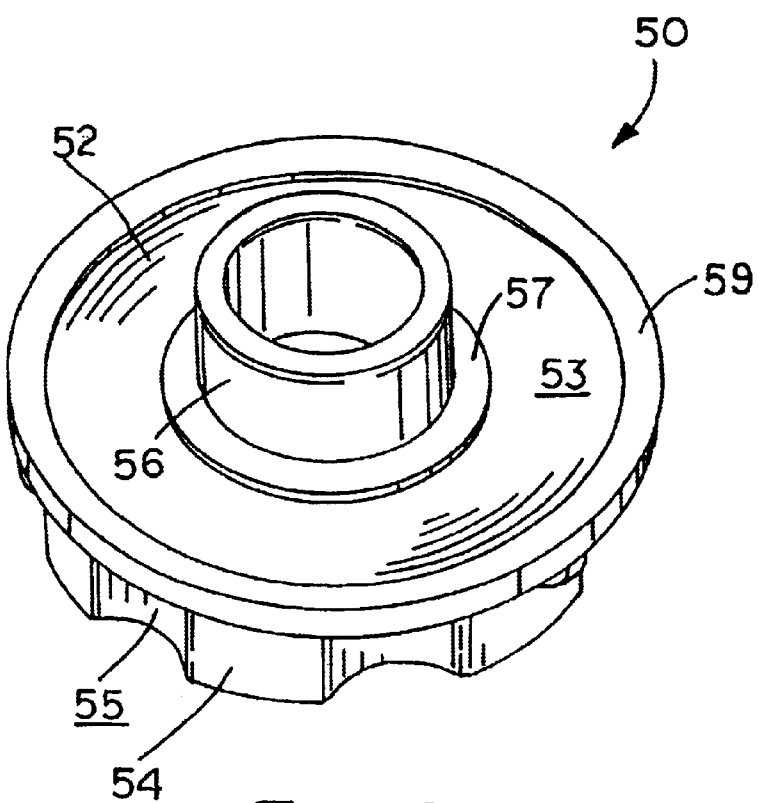
FIG. 6 is perspective view of the venting chassis of the embodiment of the venting plate of this invention shown in FIG. 4.
Figure 7:
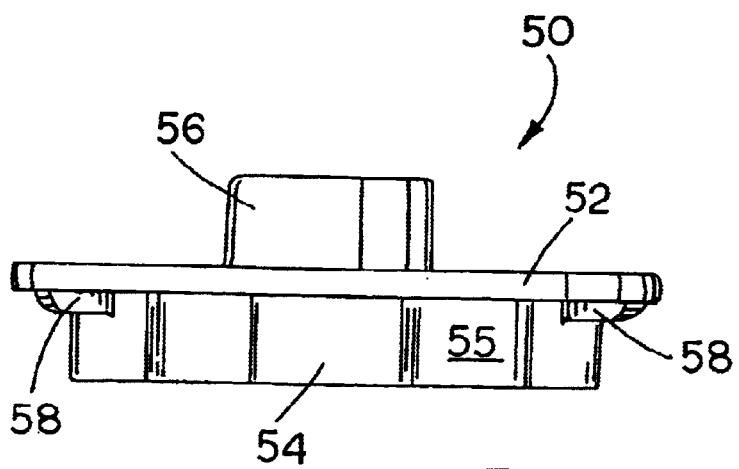
FIG. 7 is a side elevation view of the venting chassis of the embodiment of the venting plate of this invention shown in FIG. 4.
Figure 8:
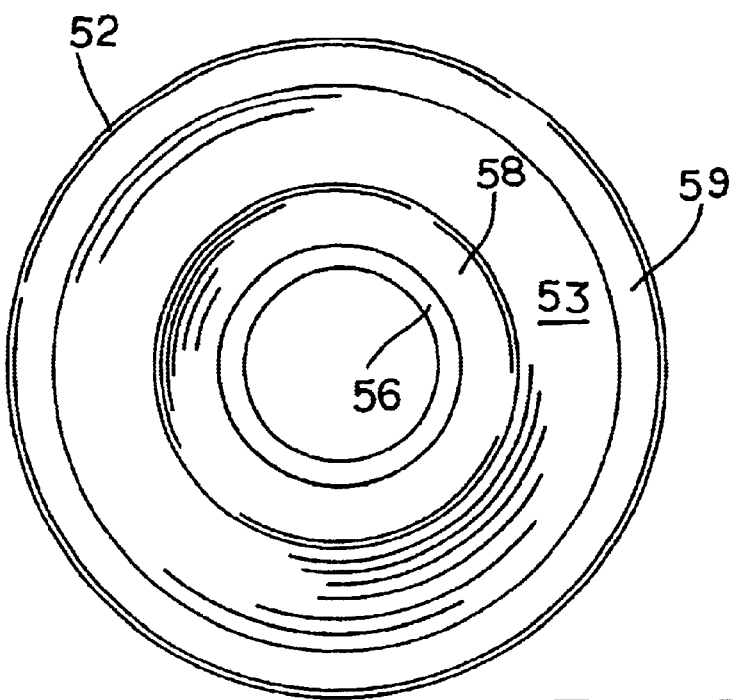
FIG. 8 is a top plan view of the venting chassis of the embodiment of the venting plate of this invention shown in FIG. 4.
Figure 9:
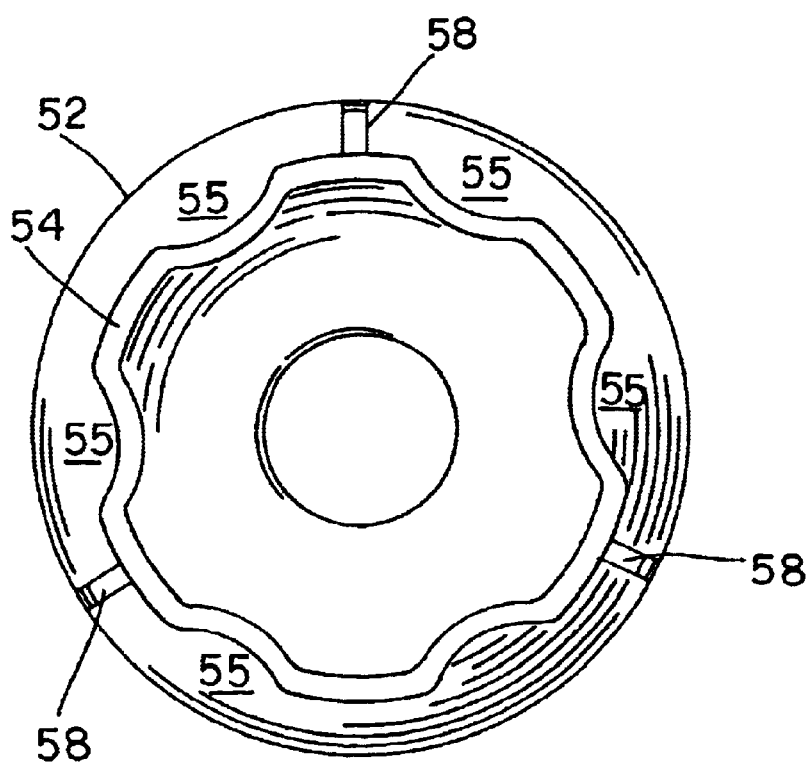
FIG. 9 is a bottom plan view of the venting chassis of the embodiment of the venting plate of this invention shown in FIG. 4.

FIGS. 4–9 illustrate a second embodiment of the venting plate of this invention (designated generally as 40), which includes generally a ceramic venting chassis 50 and a decorative three dimensional ornamentation or relief 42. As shown in FIGS. 4 and 5, ornamentation 42 is depicted as a scarecrow seated next to a hollowed out pumpkin shell. Again, ornamentation 42 is configured so that it does not obstruct the flow of exhaust air through the exhaust vent and bonded to venting chassis 50. Venting chassis 50 has the same basic design and configuration as venting chassis 30 of Venting plate 20. Venting plate 50 includes a flat plate 52, an annular skirt 54, a tubular chimney 56 and three support feet 58. Venting chassis 50 also has an annular recess 53 formed in its top surface of plate 52. Recess 53 provides an air gap between chassis 50 and ornamentation 42 to further thermally insulated ornamentation 42. Recess 53 should be at least 0.030 inches deep and 0.500 inches wide to provide a sufficient air gap between the chassis and ornamentation. Recess 53 leaves outer and inner concentric annular surfaces 57 and 59 to which ornamentation 42 is bonded. In addition, skirt 54 has six longitudinal furrows, which form six air flow inlet channels or vents 55. In this embodiment, skirt 54 is seated within the mouth of the candle so that inlet air only passes through channels 55. The inlet channels 55 columnate the inlet air flow into distinct columns of air that converge toward the flame. Columnating the air flow increases the velocity of the inlet air flow through the candle interior, which promotes improved scent flow from the candle.

Venting plates 20 and 40 each operate identically to create a physically separated concentric laminar air flow within candle interior, which stabilizes the flame and improves the efficiency of the combustion. As shown in FIG. 1 (venting plate 20 only), the venting plate sits atop of candle 2 supported by the mounting feet, such that the skirts extend downward into the candle mouth and the plates are spaced vertically above candle brim 14. In both embodiments, the exhaust vent is positioned directly above flame 8. The thermal energy generated from flame 8 creates an upward convection flow of hot exhaust air 7, which exits the candle interior through the exhaust vent. Positioning the exhaust vent directly above the candle flame focuses the convection draft of exhaust air flow 7 directly upwards, which reduces diffusion of the exhaust flow and its thermal energy. The negative pressure within the candle interior created by exhaust air flow 7 draws an inlet air flow 9 of cool ambient air underneath the plates between the plate and vessel brim 14. The skirts redirect inlet air flow 9, which enters the candle horizontally from underneath the venting plate, downward along vessel sidewall 12. For venting plate 20, inlet air passes through the space between skirt 36 and vessel brim 14., For venting plate 40, inlet air passes through six inlet channels 55, which columnate the inlet air flow into distinct columns of air which results in an increased inlet air flow velocity. The columns of inlet air move along the melted wax pool and converge at the base of the candle flame. In both embodiments, the skirts act as baffles that separate the opposing air flows (inlet and exhaust) to reduce turbulence within the interior of the vessel and stabilize the flame, which leads to a cleaner combustion process and reduced carbon residue (smoke) in the exhaust.

Figure 13:
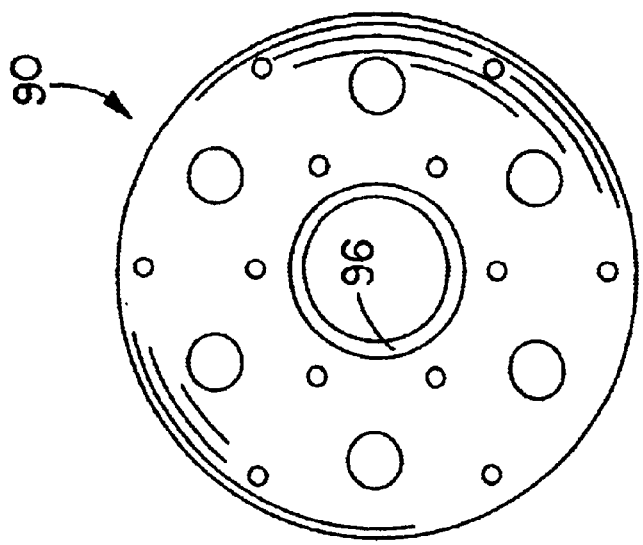
FIG. 13 is a top plan view of the venting chassis of the embodiment of the venting plate of this invention shown in FIG. 12.
Figure 12:
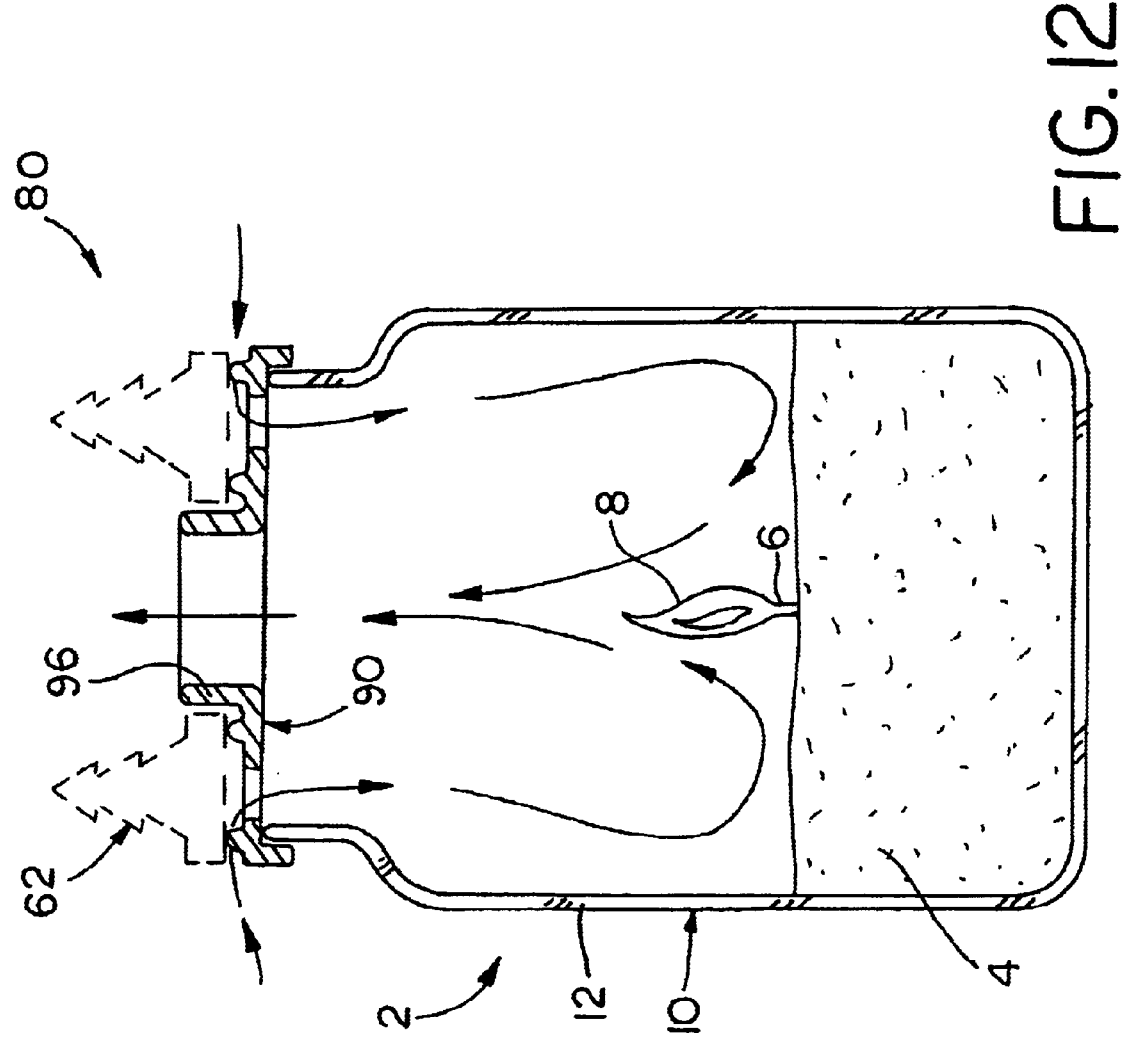
FIG. 12 is a side sectional view of a fourth embodiment of the venting plate of this invention seated atop a cylindrical containerized candle.

FIGS. 10–13 show third and fourth embodiments of the venting plate of this invention (designated generally as reference numeral 60 and 80), both of which are illustrated with the same three dimensional ornamentation (designated generally as reference numeral 62). As shown in FIGS. 10 and 11, venting plate 60 includes a ceramic venting chassis 70, which uses a conventional flat venting plate design and includes a flat disc 72 having a plurality of inlet openings or vents 71 formed around a central exhaust opening or vent 73. Disc 72 also includes a plurality of raised detent or feet 74. Feet 74 extend at least 0.250 inches above the top surface of disc 72. Ornamentation 62 is bonded to feet 74 and space the ornamentation above the top surface of plate 72 to create an air gap 75, which allows inlet air to pass between the plate and the ornamentation and enter the candle interior through inlet vents 71. The air gap between the ornamentation and disc also provides thermal insulation for ornamentation 62. As shown in FIGS. 12 and 13, venting plate 80 includes a ceramic venting chassis 90, which simply adds a chimney 96 around the exhaust vent to again shield the ornamentation from the hot exhaust air.

Venting plates 60 and 80 both function identically. Exhaust air is expelled through the central exhaust vent, which draws inlet air through the venting chassis. Inlet air passes between the ornamentation and disc and enters the candle interior through the inlet vents in the disc. The venting chassis restricts and controls the inlet and exhaust air flows into and out of the interior of the jar. The exhaust vent and the intake vents are spaced apart from each other sufficiently to facilitate separated concentric laminar air flows of exhaust and ambient air within the candle vessel to ensure that sufficient ambient air is drawn to the base of the flame. The spacing of the inlet and exhaust openings is critical to maintain separated laminar flow, while the inlet flow has sufficient downward velocity to generate the inertia force to carry the inlet flow to the base of the flame. The spacing creates an annular zone of relatively still or dead air. This band of dead air acts as a physical insulator between the inlet and exhaust air flows to reduce the turbulence caused by the direct mixing of the opposed exhaust and intake air flows.

ADVANTAGES

One skilled in the art will note several advantages of the venting plates of this invention. The venting plate of this invention employs a two piece design: chassis and relief. The two piece design separates the venting function of the chassis from the decorative function of the ornamentation. Forming the inlet vents by spacing the body of the venting plate above the vessel rim eliminates the need for additional inlet vent openings in the body of the plate. Consequently, the chassis can be ornamented with surface decorations or with elaborate three dimensional reliefs. The design of the chassis allows its entire top surface, except the area directly above the exhaust vent to be ornamented while still facilitating laminar air flow within the candle. The two piece design also simplifies production and reduces costs. Particular ornamentation can be produced in various quantities and molded to a single basic chassis configuration, which allows the venting plate be produced less expensively.

The ceramic construction of the chassis also enables the venting plate to be adorned with heat sensitive poly resin ornamentation. Poly resin ornamentation is inexpensive and easy to produce. More importantly, poly resin ornamentation can be formed and molded into three dimensional shapes and arrangements for an infinite variety of decorative genre and styles. Poly resin ornamentation, however, must be insulated from the heat generated by the candle. Constructed from ceramic materials, the chassis are inexpensive and easily produced in mass quantities and provide sufficient structural integrity to support the ornamentation. Most critically, however, ceramic materials are an ideal construction material for the chassis because of the high thermal insulating property. Ceramics are poor conductors of thermal energy. Under direct contact with a flame, ceramics will get hot, but the thermal energy will be localized in a small region of direct contact with the flame. While ceramic materials are ideal, one skilled in the art will note that other thermal insulating materials that can provide sufficient structural integrity can be employed without deviating from the teachings herein.

In two embodiment of the venting plate, the venting chassis eliminates the inlet openings in the body of the chassis. Forming inlet vents beneath the plate also ensures that the inlet air is drawn into the vessel interior as distant from the exhaust air flow as possible, thereby maximizing flow separation and allows the entire top surface of the chassis to be adorned. The use of an internal baffle to direct the inlet air flow concentrically along the sidewalls of the containerized candle ensures concentric laminar air flow within the containerized candle and separation of the inlet and exhaust air flows. The physical separation of the inlet and exhaust air flow openings is sufficient to maintain laminar flow within the containerized candle regardless of the shape or dimension of the vessel interior or the ornamentation adorning the chassis.

The design of the chassis also helps protect the ornamentation form heat damage. The chimney also provides a thermal shield for the ornamentation supported atop the chassis. Poly resin ornamentation can be damaged by the hot exhaust air from the candle, as well as from heat from the candle flame. The chimney provides a thermal shield from the hot exhaust air without significantly detracting from the aesthetic appearance of the venting plate. In addition, the air gaps created by the annular recess formed in the top surface of the chassis plate in the second embodiments of the venting plate and formed by the feet supporting the ornamentation in the third and fourth embodiments further insulates the ornamentation. The air gaps add an additional safety measure to the venting plates. Because ceramics will become extremely hot in localized areas exposed to a direct flame, the air gap prevents the direct conduction of thermal energy to the relief. This is an important feature, when the candle wick is not centered directly in the center of the jar and over the exhaust vent of the venting plate. If the wick is off centered, the chassis could be exposed to a direct flame, which may melt or ignite the relief.

It is understood that the above description does not limit the invention to the details given, but may be modified within the scope of the following claims.

I claim:

1. A venting apparatus for improving the stability and efficiency of the combustion flame of a containerized candle that includes a fuel source burnt in the flame, a wick and a vessel, which defines an interior thereof for enclosing the wick and fuel source and has an open mouth, and where the vessel includes sidewalls that terminate in a brim at the open mouth of the vessel, the venting apparatus comprising:
  a chassis and a decorative ornamentation mounted to the chassis,
  the chassis composed of a ceramic material having a thickness to thermally insulate the ornamentation from heat generated when the candle is burnt,
  the chassis includes a flat plate shaped and dimensioned to cover the open mouth of the vessel and extend over the brim, the plate having a top surface and a bottom surface and also having an exhaust vent therein for venting a flow of exhaust air from the vessel interior,
  a tubular chimney extending from the top surface of the plate around the exhaust vent for shielding the ornamentation from heat emitting from exhaust air exiting through the exhaust vent when the candle is burnt,
  a plurality of feet extending downward from the bottom surface of the plate for spacing the plate above the brim when the venting apparatus is seated atop the vessel to permit a flow of inlet air between the plate and the vessel brim, and
  an annular baffle extending downward from the bottom surface of the plate between the plurality of feet and the exhaust vent so as to extend partially downward into the open mouth of the vessel and to seat adjacent the brim of the vessel when the apparatus is seated atop the vessel for directing the flow of inlet air downward along the sidewalls of the vessel and for separating the flow of inlet air from the flow of exhaust air.

2. The apparatus of claim 1 wherein the ornamentation is mounted to the top surface of the plate around the chimney.

3. The apparatus of claim 2 wherein the top surface of the plate has an annular recess formed therein, such that along the width of the recess the top surface of the plate is spaced from the ornamentation to create an air gap therebetween, thereby further insulating the ornamentation from heat generated when the candle is burnt.

4. The apparatus of claim 4 wherein the recess formed in the top surface of the plate is at least 0.030 inches deep and is at least 0.500 inches wide.

5. The apparatus of claim 2 wherein the chimney extends at least 0.50 inches above the top surface of the plate so as to sufficiently shield the ornamentation from heat emitting from exhaust air exiting through the exhaust vent when the candle is burnt.

6. The apparatus of claim 1 wherein the thickness of the ceramic material of the chassis is at least 0.125 inches.

7. The apparatus of claim 1 wherein the ornamentation is composed of a poly resin material.

8. The apparatus of claim 7 wherein the ornamentation includes a three dimensional body.

9. A venting apparatus for improving the stability and efficiency of the combustion flame of a containerized candle that includes a fuel source burnt in the flame, a wick and a vessel, which defines an interior thereof for enclosing the wick and fuel source and has an open mouth, and where the vessel includes sidewalls that terminate in a brim at the open mouth of the vessel, the venting apparatus comprising:
- a chassis and a decorative ornamentation mounted to the chassis,
- the chassis composed of a ceramic material having a thickness to thermally insulate the ornamentation from heat generated when the candle is burnt,
- the chassis includes a flat plate shaped and dimensioned to cover the open mouth of the vessel and extend over the brim, the plate having a top surface and a bottom surface, the plate also having a central exhaust vent therein for venting a flow of exhaust air from the vessel interior and plurality of inlet vents therein spaced radially from the exhaust vent,
- a plurality of feet extending from the top surface of the plate, the ornamentation mounted to the plurality of feet and spaced over the top surface of the plate so as to create an air gap between the ornamentation and top surface of the plate so as to allow inlet air to pass through the air gap and the plurality of inlet vents to enter the candle interior when the apparatus is seated atop the candle, the air gap constituting means for further thermally insulating the ornamentation from heat generated when the candle is burnt.

10. The apparatus of claim 9 wherein the chassis also includes a tubular chimney extending from the top surface of the plate around the exhaust vent for shielding the ornamentation from heat emitting from exhaust air exiting through the exhaust vent when the candle is burnt.

11. The apparatus of claim 10 wherein the chimney extends at least 0.500 inches above the top surface of the plate so as to sufficiently shield the ornamentation from heat emitting from exhaust air exiting through the exhaust vent when the candle is burnt.

12. The apparatus of claim 9 wherein the thickness of the ceramic material of the chassis is at least 0.125 inches.

13. The apparatus of claim 9 wherein the ornamentation is composed of a poly resin material.

14. The apparatus of claim 13 wherein the ornamentation includes a three dimensional body.

* * * * *